(12) United States Patent
Gullbrand et al.

(10) Patent No.: US 10,282,965 B2
(45) Date of Patent: May 7, 2019

(54) SYNTHETIC JET DELIVERING CONTROLLED FLOW TO SENSOR SYSTEM

(71) Applicant: Intel Corporation, Santa Clara, CA (US)

(72) Inventors: Jessica Gullbrand, Hillsboro, OR (US); Melissa A. Cowan, Hillsboro, OR (US); Chytra Pawashe, Beaverton, OR (US); Feras Eid, Chandler, AZ (US)

(73) Assignee: INTEL CORPORATION, Santa Clara, CA (US)

( * ) Notice: Subject to any disclaimer, the term of this patent is extended or adjusted under 35 U.S.C. 154(b) by 94 days.

(21) Appl. No.: 14/567,625

(22) Filed: Dec. 11, 2014

(65) Prior Publication Data

US 2016/0171869 A1 Jun. 16, 2016

(51) Int. Cl.
*G01N 1/22* (2006.01)
*F15D 1/00* (2006.01)
(Continued)

(52) U.S. Cl.
CPC ......... *G08B 21/182* (2013.01); *G01N 1/2273* (2013.01); *G01N 1/24* (2013.01);
(Continued)

(58) Field of Classification Search
CPC .............................. F15D 1/0095; F15D 1/008
See application file for complete search history.

(56) References Cited

U.S. PATENT DOCUMENTS 5,488,352 A * 1/1996 Jasper ................ H01R 13/6633
280/423.1

5,894,990 A 4/1999 Glezer et al.
(Continued)

FOREIGN PATENT DOCUMENTS

WO 0058566 10/2000

OTHER PUBLICATIONS

Author:Bolzmacher et al.; Title: Robust miniaturized amplification unit for piezoelectric actuators: comparison of single crystal silicon and superelastic nickel titanium as membrane materials; URL:http://link.springer.com/content/pdf/10.1007%2Fs00542-009-1008-x.pdf; Date: 2010.*

(Continued)

*Primary Examiner* — Matthew G Marini
*Assistant Examiner* — Ruben C Parco, Jr.
(74) *Attorney, Agent, or Firm* — Finch & Maloney PLLC

(57) ABSTRACT

Techniques are disclosed for using synthetic jet technology as an air delivery device for sensing applications. In particular, a synthetic jet device is used to deliver a controlled airflow or other fluidic flow to a sensor measurement area. Such a sensing system can be used to detect accurate concentration of target features present in the ambient surroundings, such as gases, particles, solutions, mixtures, and any other environmental features that can be sensed from a controlled airflow. An example application is air quality monitoring by using one or more synthetic jet devices to deliver a known or otherwise controlled airflow to a sensing area, thereby allowing for detection of harmful or otherwise unacceptable concentrations of particulate matter, gases, or air pollutants. In some embodiments, a synthetic jet device is operatively coupled with a sensor via a flow channel in a common housing, so as to provide a controlled flow sensing system.

25 Claims, 12 Drawing Sheets

(51) Int. Cl.
*G08B 21/18* (2006.01)
*H01L 23/473* (2006.01)
*G08B 25/08* (2006.01)
*G08B 21/12* (2006.01)
*G01N 1/24* (2006.01)

(52) U.S. Cl.
CPC ............. *G08B 21/12* (2013.01); *G08B 25/08* (2013.01); *H01L 23/4735* (2013.01); *F15D 1/0095* (2013.01); *G01N 2001/242* (2013.01); *H01L 2924/0002* (2013.01)

(56) References Cited

U.S. PATENT DOCUMENTS

| | | | | |
|---|---|---|---|---|
| 6,059,046 | A * | 5/2000 | Lowry | A62C 99/0018 169/61 |
| 6,522,248 | B1 * | 2/2003 | Andres | G08B 3/10 340/511 |
| 6,587,739 | B1 * | 7/2003 | Abrams | G05B 15/02 340/12.32 |
| 6,588,497 | B1 | 7/2003 | Glezer et al. | |
| 7,252,140 | B2 * | 8/2007 | Glezer | H05K 7/20172 165/80.3 |
| 2004/0152211 | A1 | 8/2004 | Majumdar | G01N 33/54373 436/518 |
| 2007/0069905 | A1 * | 3/2007 | Wang | G08B 17/117 340/632 |
| 2007/0127210 | A1 | 6/2007 | Mahalingam et al. | |
| 2008/0299013 | A1 * | 12/2008 | Trieu | B01L 9/527 422/400 |
| 2010/0043900 | A1 | 2/2010 | Xu et al. | |
| 2010/0065260 | A1 | 3/2010 | Sakamoto et al. | |
| 2010/0229658 | A1 * | 9/2010 | Glezer | G01N 1/2273 73/863.81 |
| 2012/0180457 | A1 | 7/2012 | Liu et al. | |
| 2012/0298769 | A1 * | 11/2012 | Heffington | B64C 23/04 239/102.1 |
| 2014/0134053 | A1 | 5/2014 | Mayer et al. | |

OTHER PUBLICATIONS

Title: "The Condensed Guide to Silicon Circuit Boards"; Date: Jul. 23, 2013; URL: http://www.eejournal.com/article/20130723siliconcirc/.*
Parvis, et al., "Electrostatically driven synthetic microjet arrays as a propulsion method for micro flight," Part II: microfabrication and initial characterization. Microsyst Technol (2005) (11). pp. 1292-1300.
Gimeno, et al., "Synthetic jets based on micro magneto mechanical systems for aerodynamic flow control," IP Address: 192.55.54.42. Downloaded from iopscience.iop.org on Oct. 30, 2014 at 21:05. Journal of Micromechanics and Microengineering, published May 21, 2010. 8 pages.
Pimpin, et al., "Micro Electrostrictive Actuator With Metal Compliant Electrodes for Flow Control Applications," IEEE, 2004. pp. 478-481.
Mallinson, et al., "Synthetic jet actuators for flow control," Part of the SPIE Conference on Electronics and Structures for MEMS, SPIE vol. 3891. Oct. 1999. 11 pages.
Mahalingam, et al., "Thermal Management Using Synthetic Jet Ejectors," IEEE Transactions on Components and Packaging Technologies, vol. 27, No. 3, Sep. 2004. p. 439-444.
Roman, Max, "Modeling, Design, and Fabrication of Pulsed Fluidic Micro-Actuators," A Dissertation submitted to New Jersey Institute of Technology, Jan. 2006. 113 pages.
Li, Shuo, "A Numerical Study of Micro Synthetic Jet and Its Applications in Thermal Management," A Thesis submitted to G.W. Woodruff School of Mechanical Engineering Georgia Institute of Technology, Dec. 2005. 267 pages.
"Synthetic jet," URL: http://en.wikipedia.org/wiki/Sy . . . Downloaded from the Internet on Nov. 13, 2014. 3 pages.
Mahalingam, et al., "synthetic jets for forced air cooling of electronics," ElectronicsCooling, vol. 13, No. 2. May 2007. 6 pages.
International Search Report and Written Opinion received for International Application No. PCT/US2015/059894, dated Feb. 29, 2016, 12 pages.
Extended European Search Report received for EP application No. 15867660.1, dated Jun. 28, 2018. 9 pages.

* cited by examiner

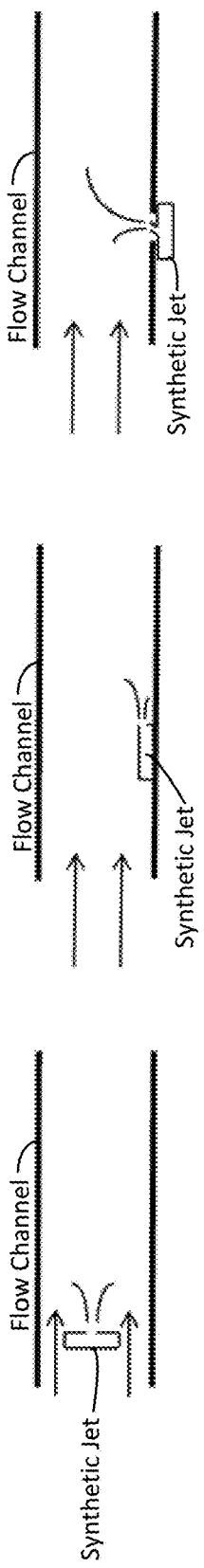

SYNTHETIC JET DELIVERING CONTROLLED FLOW TO SENSOR SYSTEM

BACKGROUND

As is known, synthetic jet technology can be used to generate fluid and air flow. A synthetic jet device, sometimes referred to as a synthetic jet ejector or synthetic jet pump, generally includes a vibrating membrane in a cavity with an orifice. The vibrating membrane generates puffs of fluids (e.g., vortices), which are expelled through the orifice. A jet flow is generated by entraining the surrounding medium such as ambient fluid or air in the stream of vortices. The surrounding medium depends on the application. For example, the surrounding medium is ambient air in the case of synthetic jet air mover applications used for cooling in electronic applications (such as LED and microprocessor cooling). In such cases, the fluid flow actuated by the vibrating membrane is generally referred to as the primary jet flow, and the entrained ambient air is the secondary flow. In operation, the vortices created by the primary jet flow result in entrainment of ambient air. Depending upon the operation needs, the primary jet flow can entrain and remove hot air, entrain cool ambient air, or a combination thereof. Synthetic jet technology has also been used for controlling airflow in aircraft to, for example, reduce drag, enhance lift and improve maneuverability.

BRIEF DESCRIPTION OF THE DRAWINGS

FIGS. 5l-r illustrate further example jet and flow channel configurations that can be used for a synthetic jet sensing system, in accordance with an embodiment of the present disclosure.

DETAILED DESCRIPTION

Figure 1A:
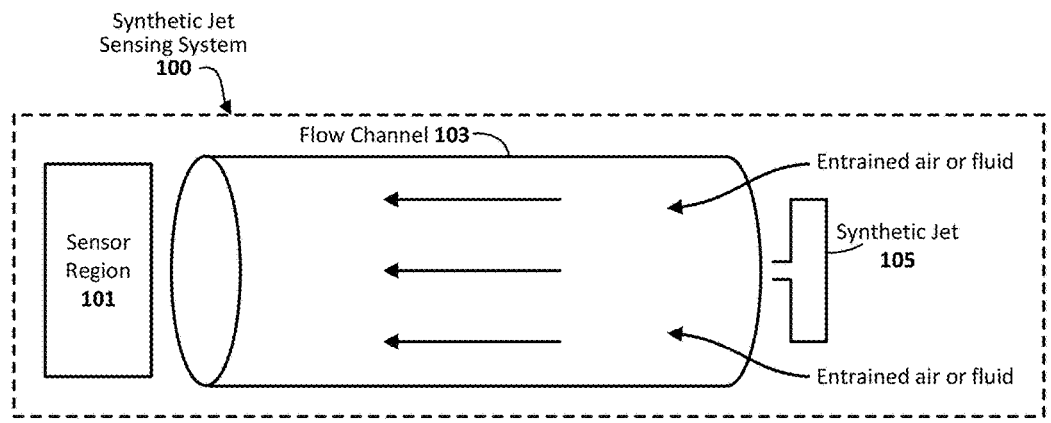
FIG. 1a-d each illustrates a synthetic jet sensing system configured in accordance with an embodiment of the present disclosure.

Techniques are disclosed for using synthetic jet technology as an air delivery device for sensing applications. In particular, a synthetic jet device is used to deliver a controlled airflow or other fluidic flow to a sensor measurement point, area, or volume. Such a synthetic jet based sensing system can be used to detect accurate concentration of target features present in the ambient surroundings of the system, such as gases, particles, solutions, mixtures, and/or any other ambient or local feature that can be sensed from a controlled airflow. An example application is air quality monitoring by using one or more synthetic jet devices to deliver a known or otherwise controlled airflow to a sensing region, thereby allowing for detection of harmful or otherwise unacceptable concentrations of particulate matter, harmful gases (e.g., sulfur oxides and nitrogen oxides), or other such air pollutants. In some embodiments, a synthetic jet device is packaged or otherwise integrated with a sensor array in a common package or housing, wherein there is a flow channel between the synthetic jet and the sensor array, so as to provide a controlled flow sensing system. As will be appreciated in light of this disclosure, such a system can be configured to deliver a controlled flow to the sensor for accurate determination of target features or concentrations.

General Overview

A significant health concern comes from small particles suspended in the air, sometimes referred to as particulate matter, which can lead to respiratory and cardiovascular issues. The Environmental Protection Agency (EPA) has recommendations on safe and unhealthy exposure limits. These limits are described as ranges of concentrations for particulate matter and gases. There are environmental sensor systems on the market today. These solutions are fairly large and have fans or blowers installed to deliver a forced airflow. However, fans and blowers are very inefficient air movers, particularly if they are to be scaled down to very small sizes such as millimeter scale. Other environmental protection solutions use thermal resistance to generate a natural convection flow, which does not deliver a known or controlled airflow. A synthetic jet device can be used to deliver relatively large flow rates for very small devices. However, synthetic jet devices have historically been used in other types of applications such as cooling of electronics.

Thus, and in accordance with an embodiment of the present disclosure, a new usage for synthetic jet devices is provided. In particular, synthetic jets can be used for delivering controlled flows to sensor locations, especially in space and power constrained devices, such as wearable computing devices or so-called wearables, smartphones, tablets, and other such mobile computing devices. Note, however, that the techniques provided herein need not be limited to mobile computing platforms and can be used in any computing platform or other sensing system. The synthetic jet devices allow for delivering a known flow rate and therefore volume of air (or fluid) to the sensing region for accurate concentration measurements of one or more target features. In some embodiments, one or more synthetic jet devices are integrated with one or more sensors into a common package or housing so as to provide a sensing system, such as a system-on-chip (SOC). Numerous variations and configurations will be apparent in light of this disclosure.

The sensor or sensor array with which the synthetic jet(s) are packaged or otherwise used can be configured to sense any desired target ambient feature or features, which can vary depending on the given sensing application. The target feature may be, for example, ambient air quality (e.g., sulfur and nitrogen oxides), particulate matter, radioactive material, or a particular gas, solution, mixture, or compound, to name a few examples. In any such cases, each of the synthetic jet and sensing devices can be scaled down for integration into small form factors, wherein the synthetic jet devices provides a controlled airflow via one or more flow channels to the sensors so as to allow for accurate concentration measurements of the target feature(s). Note that the synthetic jet devices are not limited to air movement, as they can also generate jet movement of any fluid.

One specific example embodiment can be implemented with a mobile computing device to provide a personal air quality monitoring system that alerts the user to unacceptable concentrations of specific air pollutants or otherwise poor quality air. In one such embodiment, the synthetic jet based sensing system can be configured to periodically sample the ambient air wherever the user goes, and an alert message can be provided to the user. Changes in geolocation of the user can also be used to trigger sampling of the ambient air. In any case, the alert message may be, for example, a text or email message, a pop-up window, or an audible chime that the user has previously associated with the sensing application (e.g., a two-tone chime indicates an unacceptable concentration or sulfur oxide has been detected). In some cases, the user can configure the system with respect to, for example, the target features to be detected as well as the detection thresholds that must be exceeded for an alert to be given. Numerous such messaging and user interface schemes can be used to improve the user experience, as will be appreciated in light of this disclosure.

Another specific example embodiment is a distributed sensor system, such that different nodes of the system include a sensor system as provided herein. For instance, in one specific example case, one or more synthetic jet based sensors as provided herein can be distributed or otherwise deployed on a communication network so as to provide accessible sensor nodes that can provide sensor data to a central location or to any entity capable of accessing the sensor node(s). Such an embodiment may be implemented, for example, in the context of a so-called Internet of Things (IoT) configuration to provide the one or more sensor nodes or other such distributed sensor system. Further note that in such an IoT system, the device could be integrated in a fixed sensor node deployed at a particular location and is not necessarily mobile.

System Architecture

FIG. 1a illustrates a synthetic jet sensing system 100 configured in accordance with an embodiment of the present disclosure. As can be seen, the system 100 includes a sensor 101 operatively coupled with a synthetic jet device 105 via a physical flow channel 103. Each of these components 101, 103, and 105 can be implemented, for example, using discrete components that are populated on a printed circuit board or other suitable substrate. The substrate may be contained in a housing or package so as to effectively provide an integrated circuit solution. Alternatively, each of the components 101, 103, and 105 can be implemented using semiconductor materials and standard processing to provide an integrated circuit solution, as will be appreciated in light of this disclosure. In any such cases, the physical flow channel 103 operatively couples with the output of the synthetic jet device 105, such that ambient air (or fluid, as the case may be) is entrained and effectively sucked into the flow channel 103 and directed to the sensor region 101. The flow rate of the entrained air or fluid can be adjusted or otherwise controlled based on the needs of the given sensing application, so as to provide a controlled flow for accurate concentration detection by the sensor region 101. For instance, a controlled flow with different flow rates can be delivered by altering the amplitude and/or shape of the drive signal, the oscillation frequency and/or the oscillation shape of the membrane. For an electrostatically driven device, this may include, for example, changing the voltage amplitude of the drive signal or the shape of the drive signal (e.g., using sinusoidal, triangle, square wave signals, or other such signal shapes), and the oscillating frequency. The sensor region 101 can include any type of sensor suitable for a given sensing application. Example sensors include optical sensors, microelectromechanical systems (MEMS) resonance sensors, electromechanical sensors or transducers, metal oxide sensors, electrochemical sensors, radiation sensors, pollutant sensors, gas sensors, to name a few. In a more general sense, the sensor region 101 can be configured with any sensing technology capable of sensing the presence of a target material when presented within a controlled flow by operation of the synthetic jet device 105 via the flow channel 103.

Figure 1B:
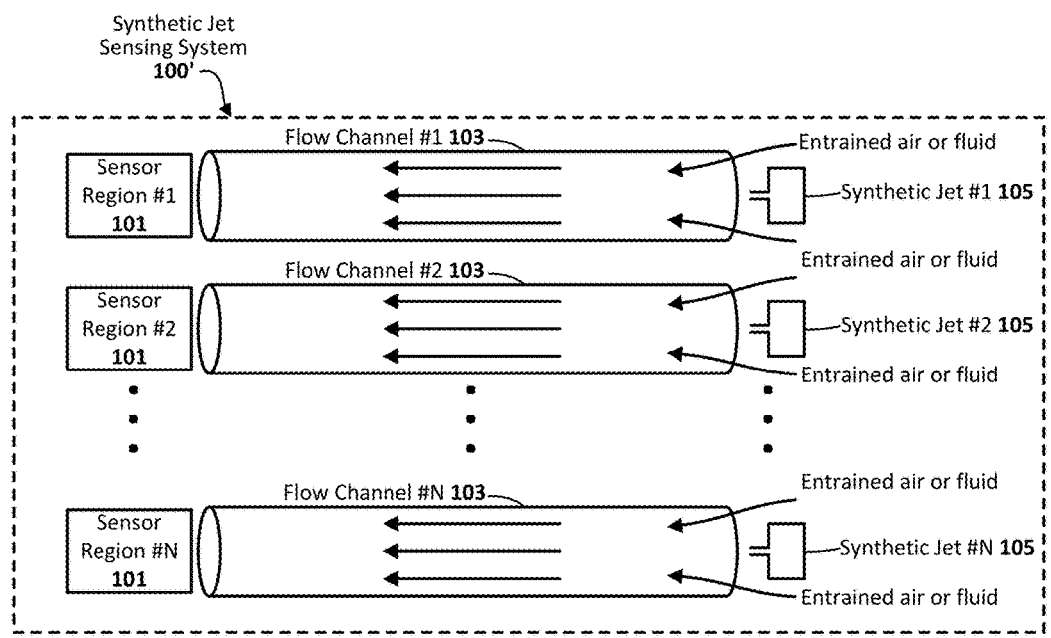

FIG. 1b illustrates a synthetic jet sensing system 100' configured in accordance with another embodiment of the present disclosure. As can be seen, this system 100' is similar to that of system 100 in FIG. 1a, except that there are a plurality of flow channels 101 (flow channel #1 through #N) operatively coupling an array of synthetic jet devices 105 (device #1 through #N) to an array of sensor regions 101 (sensor region #1 through #N). As will be appreciated, the sensor regions 101 may each include the same type of sensor in some embodiments, while other embodiments may have each of the sensor regions 101 configured with a different type of sensor (e.g., one for detecting sulfur oxides, another for detecting nitrogen oxides, another for detecting carbon monoxide, etc). Such an array-based synthetic jet sensing system 100' may also be contained within a package or housing so as to provide an integrated solution, just as with system 100.

Figure 1C:
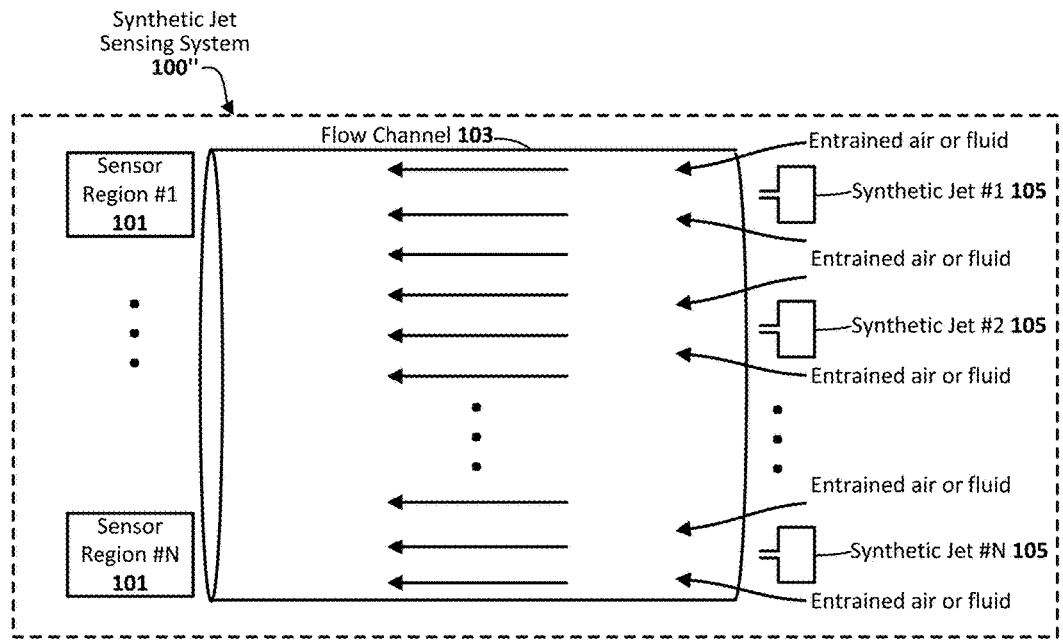

FIG. 1c illustrates a synthetic jet sensing system 100" configured in accordance with another embodiment of the present disclosure. As can be seen, this system 100" is similar to that of system 100' in FIG. 1b, except that there is a single flow channel 103 operatively coupling an array of synthetic jet devices 105 (device #1 through #N) to an array of sensor regions 101 (sensor region #1 through #N). As previously explained with respect to FIG. 1b, the sensor regions 101 may each include the same type of sensor in some embodiments, while other embodiments may have each of the sensor regions 101 configured with a different type of sensor (e.g., one for detecting sulfur oxides, another for detecting nitrogen oxides, another for detecting carbon monoxide, etc). Note that while this example embodiment shows N sensors 101 and N synthetic jet devices 105, other embodiments may have a fewer or more sensors 101 than synthetic jet devices 105. Such an array-based synthetic jet sensing system 100" may also be contained within a package or housing so as to provide an integrated solution, just as with system 100.

Figure 1D:
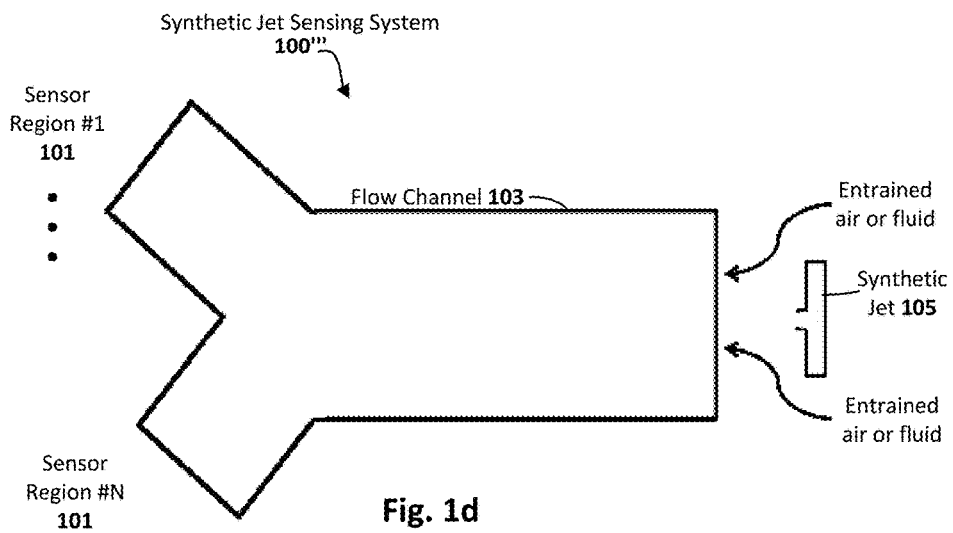

FIG. 1d illustrates a synthetic jet sensing system 100'" configured in accordance with another embodiment of the present disclosure. In this example case, the flow channel 103 is fed from a single synthetic jet device 105 and is divided up into two or more different channels at the other end, each channel delivering a controlled flow to a corresponding sensor 101 (sensor region #1 through #N). As previously explained with respect to FIG. 1b, the sensor regions 101 may each include the same type of sensor in some embodiments, while other embodiments may have each of the sensor regions 101 configured with a different type of sensor (e.g., one for detecting sulfur oxides, another for detecting nitrogen oxides, another for detecting carbon monoxide, etc). As further previously explained, such an array-based synthetic jet sensing system 100'" may also be contained within a package or housing so as to provide an integrated solution, just as with system 100.

Numerous other configurations will be apparent in light of this disclosure wherein any number of synthetic jet devices 105 is operatively coupled to one or more sensors 101 via one or more flow channels 103. Clusters of synthetic jet devices 105 may feed a single flow channel 103 that splits into a plurality of channels each going to one or more sensors 101. Likewise, clusters of sensors 101 can be feed from one or more flow channels 103 each of which is in turn feed by one or more synthetic jet devices 105. The present disclosure is intended to cover all such permutations.

Figure 7:
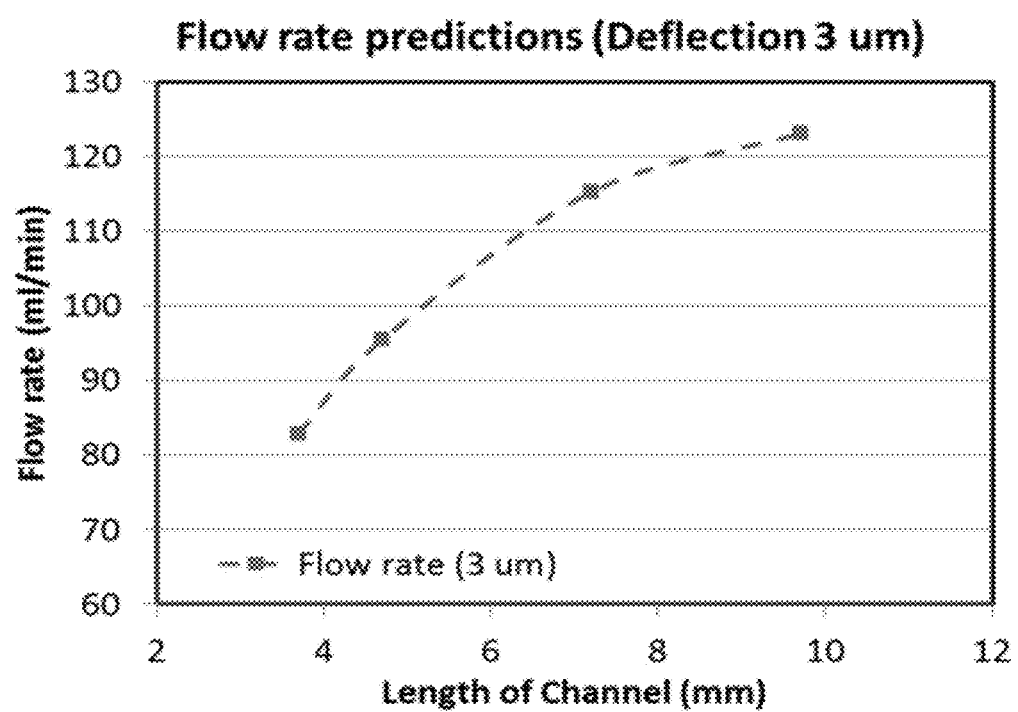
FIG. 7 illustrates flow rate as a function of flow channel length, where the diameter of the synthetic jet device is 1 mm and the flow channel 2 mm, in accordance with an embodiment of the present disclosure.

The instantaneous velocity contour (m/s) of the channel flow generated can be imaged as is sometimes done, and tuned accordingly for a given application. In general, the flow through the flow channel 103 can be steady, making it ideal for generating a controlled flow at the sensing region 101. In FIG. 7, the airflow generated in a 2 mm diameter flow channel by a 1 mm synthetic jet device 105 where the membrane vibrates with an amplitude of 3 μm is shown for different lengths of the flow channel 103. As can be seen, the longer the flow channel 103, the greater the flow rate, in this particular example.

Figure 2:
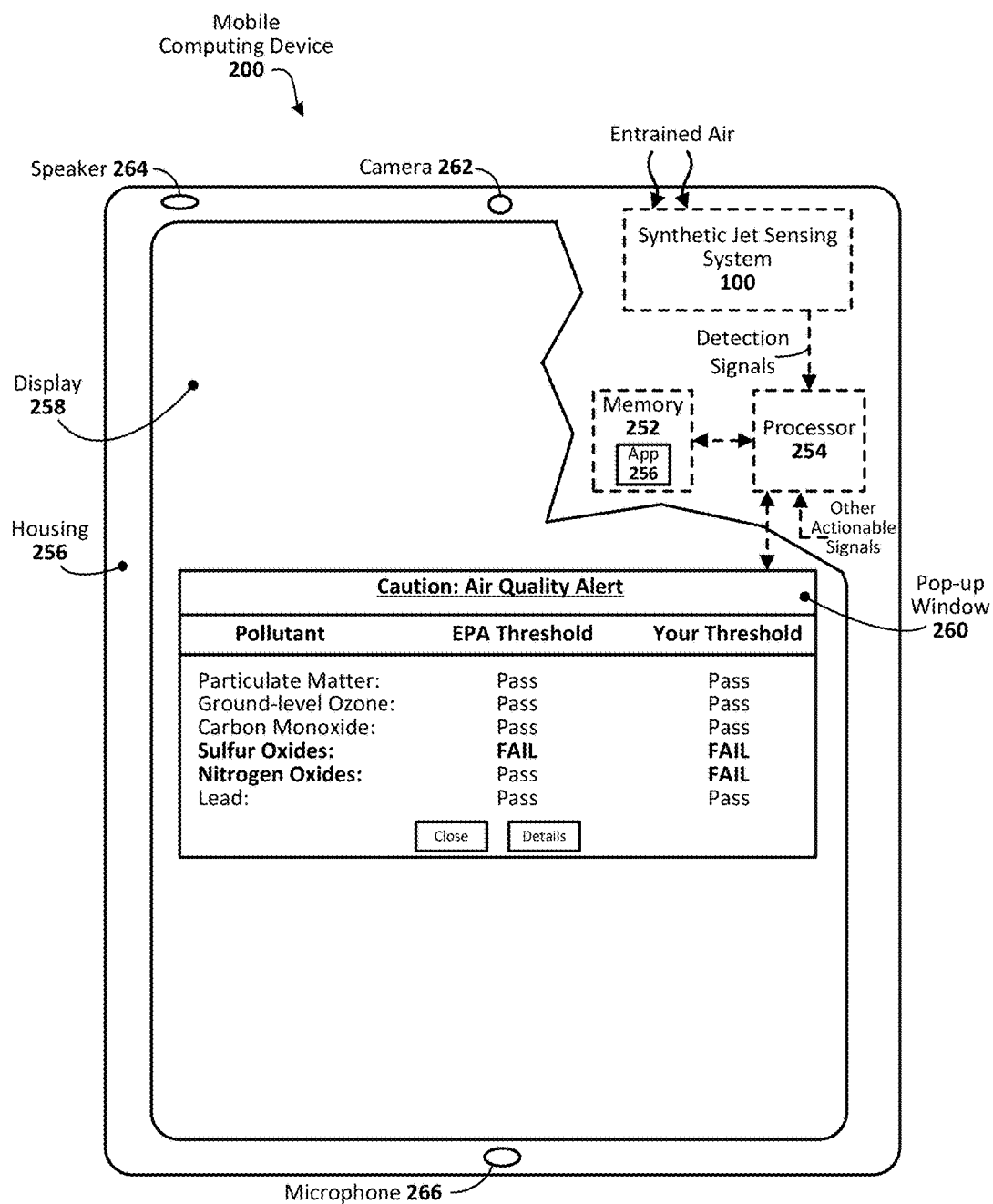
FIG. 2 illustrates a mobile computing device configured with a synthetic jet sensing system, in accordance with an embodiment of the present disclosure.

As previously explained, synthetic jet sensing systems such as 100 (from this point forward, assumed to include any of its variants, such as 100', 100'', 100''', and other such embodiments and configurations that will be apparent in light of this disclosure) can be implemented in any computing system, whether it be a stationary computer system in a laboratory or office setting or a mobile computing platform. As will be further appreciated, the system may be a dedicated sensing system, and need not be a general computing system. Given the ubiquitous nature of mobile computing devices, they are particularly well-suited for being configured to monitor for air pollutants using the techniques as provided herein. In any such case, the synthetic jet sensing system can be operatively coupled with a host computing system, whether by an external coupling such as a USB cable or wireless communication link or some other suitable communication medium that allows for data exchange, or by being directly integrated within the architecture of a computing device. Any number of such external and internal configurations will be apparent in light of this disclosure. FIG. 2 illustrates one such example configuration.

As can be seen, FIG. 2 shows a mobile computing device 200 configured with a synthetic jet sensing system 100, in accordance with an embodiment of the present disclosure. The computing device 200 can be, for example, a smartphone, tablet computer, laptop computer, or wearable computer (e.g., wrist-watch, eye-glasses, jewelry, or clothing based computing systems), and may include any standard componentry normally included in such computing devices. Alternatively, the device 200 can be a dedicated mobile sensing system, also configured with typical computing capability, but more particularly geared toward sensing applications rather than general-purpose computing. As will be appreciated, not all of the features depicted need to be included in every embodiment. For instance, while a smartphone or tablet may include a microphone and speaker, a wearable computing device may not necessarily have such features. To this end, the depicted computing device 200 is only provided as an example embodiment, from which numerous other embodiments and permutations will be apparent in light of this disclosure.

In this example case, the device 200 includes a housing 256 that supports a display 258 (touchscreen or other suitable display), a camera 262 for taking images and video, a speaker 264 for aural presentation of content accessible or otherwise presentable via the device 200, and a microphone 266 for receiving verbal commands or communications from a user. In addition, the device 200 further includes a processor 254 that is operatively coupled to a memory 252 that may include various digital files (e.g., documents, photos, etc) as well as instructions and applications such as app 256. As can further be seen, the processor 254 is configured to receive detection signals from the system 100 integrated with device 200. The processor 254 may also be configured to receive any other actionable signals, such as geolocation signals from a global positioning system (GPS) receiver oftentimes included in mobile computing devices such as smart phones, tablets and specialized computing devices. As previously explained, such geolocation signals can be used to track the geographic location of the device and to inform the sampling process of device 100. Other typical computing device componentry is not shown but will be apparent, such as wireless communication modules, co-processors, graphics processors, operating system and drivers.

In this example case, app 256 provides a user interface that allows the device 200 to effectively interact with the synthetic jet sensing system 100, as will be appreciated. In operation, the system 100 is configured to continuously or periodically sample the local or ambient air by entraining that air by virtue of the synthetic jet action. In some cases, the entrained air may be pulled into the system 100 via a grill or inlet port provided in the housing 256. In some case, the inlet port can be the same port, for instance, as the one provided for the speaker 264 or the microphone 266, if a dedicated inlet port for sensing is not desired. In any case, ambient air can be entrained and sampled by the sensor(s) of the system 100. The resulting detection signal is then provided to the processor 254, which is programmed or otherwise configured by virtue of app 256 to analyze the detection signals to determine whether a given threshold has been exceeded or otherwise satisfied with respect to a target feature that has been sensed.

If a detection threshold is met, the app 256 further executes to output a pop-up window 260 thereby providing an alert to the user. In this example case depicted in FIG. 2, the target features to be sensed or otherwise tested for include a plurality of typical pollutants regulated or otherwise monitored by the EPA, including particulate matter (sometimes referred to as PM), ground-level ozone, carbon monoxide, sulfur oxides, nitrogen oxides, and lead. In some such embodiments, the pop-up window 260 will only appear if there is an alert condition detected. In other embodiments, the pop-up window 260 may also be manually called to appear so as to allow the user to view the current detections. In this example case, only pass/fail data is presented to the user. In other embodiments, actual amounts of the target features detected can be presented. In the example user interface shown, the user may select (e.g., via an appropriately placed finger tap or mouse click) the Details UI control feature to see further details about the reported features (such as specific concentrations detected and the given thresholds, as well as links to information about the pollutant). Once the user is done viewing the report, the Close UI control feature may be selected to close the pop-up window 260.

Further note that the app 256 is programmed to allow the user to set personal thresholds for each of the target features. This may be helpful, for instance, if the user is particularly sensitive to a given pollutant and therefore wishes to set more stringent thresholds, so as to be given earlier alerts when appropriate. In this example scenario, two of the six target features are reporting as having exceeded thresholds set by at least one of the EPA and the user. In particular, the amount of sulfur oxides has exceeded the thresholds set by both the EPA and the user, and the amount of nitrogen oxides has passed the EPA threshold but exceeded the tighter threshold set by the user. Numerous other scenarios and reporting schemes will be apparent in light of this disclosure.

Methodology for Reporting Detections

Figure 3:
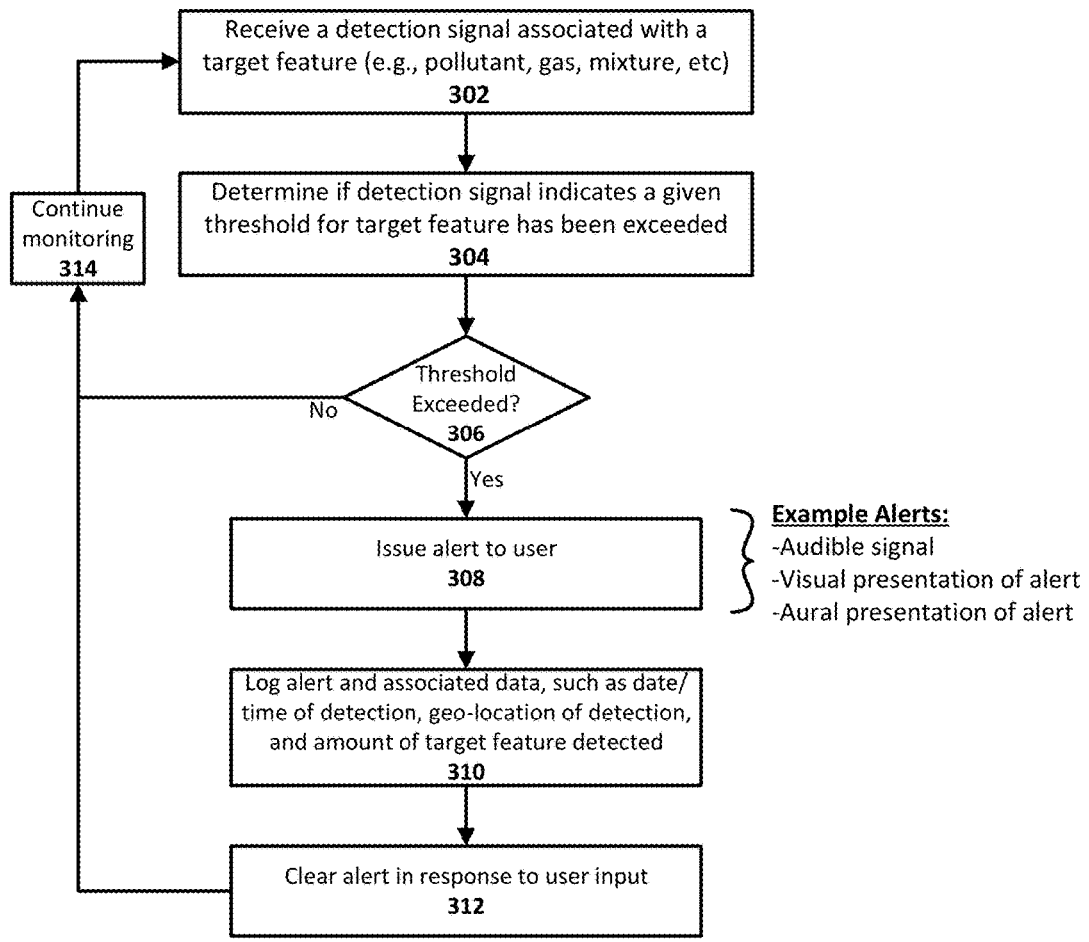
FIG. 3 illustrates a methodology for receiving and processing detection signals from a synthetic jet sensing system, in accordance with an embodiment of the present disclosure.

FIG. 3 illustrates a methodology for receiving and processing detection signals from a synthetic jet sensing system, in accordance with an embodiment of the present disclosure. This methodology may be implemented, for example, by the app 256 shown in FIG. 2, although numerous other embodiments will be apparent in light of this disclosure. The application 256 may be implemented using any instruction set (e.g., C, C++, Basic, etc) encoded on a computer program product such as memory 252 (e.g., one or more read-only memory devices, random access memory devices, flash memory devices, and/or any other suitable non-transient memory device), then when executed by one or more processors causes the methodology to be executed or otherwise carried out.

The method includes receiving 302 a detection signal associated with a target feature (e.g., pollutant, gas, mixture, etc), and determining 304 if the detection signal indicates a given threshold for the target feature has been exceeded. The detection signal can be, for example, a binary signal that is either in a first state (e.g., logic low) or a second state (e.g., logic high). In one such case, the first state indicates that the concentration of the target feature in the ambient air is below the given threshold(s), and the second state indicates that the concentration is above the given threshold(s). Alternatively, the detection signal can be a voltage level within a min-max range of the sensor device output, wherein the output voltage level can be correlated to a concentration level of the target feature in the ambient air. In a more general sense, the detection signals can be any output signal from a sensor output, or derived from a sensor output, that includes or otherwise implies at least one of detection and concentration level of the target feature. Numerous such detection signals and signal processing schemes will be apparent in light of this disclosure, and the present disclosure is not intended to be limited to any particular type.

The method continues with determination at 306 as to whether the threshold has been exceeded. If not, then the method continues with continuing monitoring at 314. As previously explained, this continued monitoring can be carried out in a continuous fashion (e.g., always-on, always monitoring). Alternatively, the monitoring can be carried out in a periodic fashion, such as according to a predefined sampling schedule and/or based on movement of the user from one geographic location to another (e.g., trigger new sampling session of ambient air if the user moves more than 500 feet from current location, or some other detectable change in geographic location).

If, on the other hand, the determination at 306 as indicates that the threshold has been exceeded, the method continues with issuing 308 an alert to the user. One example alert can be, for instance, an audible signal such as a chime or tone sequence indicative of a specific detection (e.g., a three-chime bell equals a ground-level ozone detection, while a high pitched repetitive tone equals a carbon monoxide detection). Another example alert may be a visual presentation of the alert, such as the one shown in FIG. 2 or some other depiction that the user can associate with a detection of a target feature in the ambient surroundings. Another example alert is an aural presentation of the alert, such as pre-recorded expression via the speaker of the sensing device that a target feature has been detected (e.g., "A high concentration level of sulfur oxides has been detected. A report has been emailed to you."). Another example alert is a haptic response (e.g., vibration of device) provided by a piezoelectric actuator or some other suitable element. Numerous communication schemes can be used to convey the alert, as will be appreciated.

The method may further include logging 310 the alert and associated data, such as date/time of detection, geo-location of detection, and amount of target feature detected. Such a log can be maintained in a memory of the sensing device itself and/or in a remote repository or storage (e.g., cloud-based storage used in conjunction with the app 256, or some other online storage facility). In some cases, where the target feature detected is critical (e.g., radiation), the logging at 310 may further include automatic reporting of the detection and related data to a central authority or governmental agency (e.g., EPA, Federal Bureau of Investigation, local police, etc).

The method may continue with clearing 312 the alert in response to user input, such as by selecting the Close UI control feature shown in FIG. 2. Alternatively, the alert may clear automatically upon mitigation of the offending target feature (because the target feature is no longer present in a concentration that exceeds the given threshold). As can be further seen, the method may continue monitoring as indicated at 314. Note that this continued monitoring can take place regardless of whether or not the alert is cleared, in accordance with some embodiments.

Synthetic Jet Structure

Figure 4:
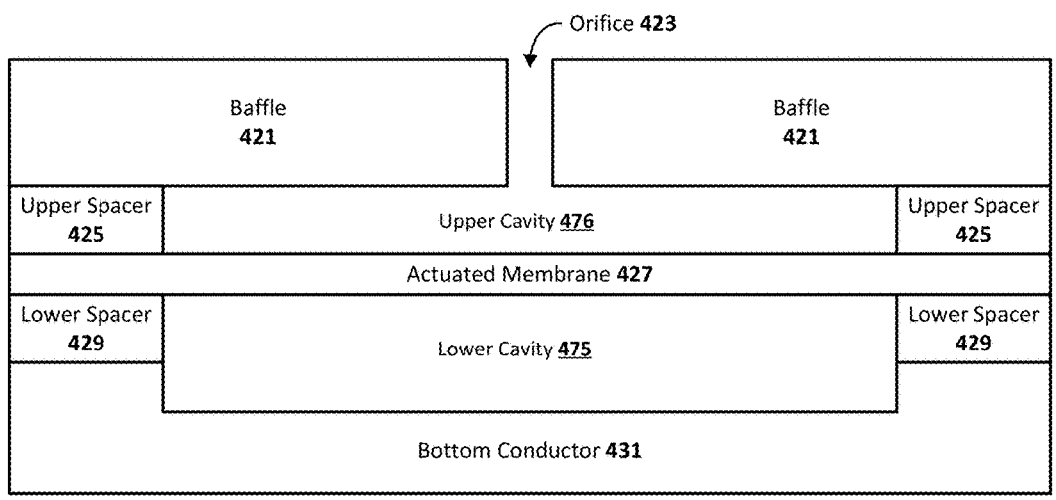
FIG. 4 illustrates an integrated synthetic jet device configured in accordance with an embodiment of the present disclosure.

FIG. 4 illustrates an integrated synthetic jet device configured in accordance with an embodiment of the present disclosure. As can be seen, the synthetic jet structure of this example embodiment includes a bottom conductor 431 spaced from an actuated membrane 427 by way of a lower spacer 429, so as to define a lower cavity 475. In addition, a baffle 421 defining an orifice 423 is spaced from the actuated membrane 427 by way of an upper spacer 425, so as to define an upper cavity 476. In operation, as the membrane 427 is driven into vibration, the membrane displacement pulls the fluid, air in one example case, into the cavity 476 and then pushes it out through the orifice 423 to create "puffs" (e.g., vortices) of air that then entrain surrounding air to induce formation of a jet flow.

The actuated membrane 427 in this example case is a conductive circular membrane that is electrostatically actuated (shown is cross-section in FIG. 4). The lower spacer 429 and upper spacer 425 can be implemented, for example, with oxides or any other suitable non-conductive or insulating material. The baffle 421 can also be implemented with an insulating or semiconductive material such as, for example, silicon or ceramic, although any number of other suitable materials can be used. For instance, in still other embodiments, the upper spacer 425 can be conductive, as can be the baffle 421 (they need not be insulating). In a more general sense, any materials can be used to implement the various features of the synthetic jet device (e.g., plastics, ceramics, metals, insulators), so long as a bias or drive signal can be applied to cause oscillation of the membrane 427. In one specific embodiment, the upper and lower spacers (429 and 425) are insulators, so as to isolate the conductive membrane 427 from the lower conductor 431 and the baffle 421. In other embodiments, such as those employing piezoelectric or electromagnetic actuation, the bottom/top spacers 429 and 425 may be conductive, as will be appreciated.

The bottom conductor 431 can be any suitable conductive material, such as polysilicon, copper, aluminum, platinum, doped silicon, or other conductive materials. For example, the bottom conductor may be implemented with silicon doped to be conductive, or a patterned metal layer such as copper or aluminum on a base substrate of some suitable material such as silicon or silicon oxide.

Such a synthetic jet device can be micro-fabricated and scaled to any dimensions, such as micro-scale or larger, depending on the sensing application and the volume of air or fluid to be moved to the sensing area. As technology progresses, nano-scale and smaller configurations can be implemented as well, using the principles provided herein and as will be appreciated. To scale the synthetic jet structure to dimensions of 1 mm or smaller in diameter, micro-fabrication techniques can be used such as those used to make commercial MEMS devices. For example, an electro-statically actuated membrane can be fabricated using MEMS or wafer bonding process flows.

In this example embodiment, the membrane 427 is conductive and is used as an electrode. To this end, the membrane 427 itself may be implemented with conductive material, or with non-conductive material that is metalized or otherwise coated with a conductive material on its surface or an appropriately doped semiconductor. In a similar fashion, the bottom conductor 431 itself may be implemented with conductive material, or with non-conductive material that is metalized or otherwise coated with a conductive material on its surface or an appropriately doped semiconductor. Note that such conductive coatings can be disposed in a pattern (e.g., patterned metal electrodes) and need not necessarily cover the entire area of the bottom conductor 431 or membrane 427. In any such cases, application of an AC voltage signal across the membrane 427 and bottom conductor 431 drives the membrane into vibration and/or resonance.

In some embodiments, the membrane 427 can be built-up from (using deposition techniques, such as epitaxial growth, spin coating, chemical vapor deposition, or other suitable deposition techniques) or otherwise bonded to the bottom conductor 431 via the non-conductive spacers 429 so as to form lower cavity 475 and allow for movement of the membrane 427. The upper cavity 476 with orifice 423 can be formed, for example, through wafer bonding or sacrificial MEMS processes. This upper cavity 476 can be hermetically sealed to the edges of the membrane 427 by way of spacers 425 to ensure the fluid (air in this example case) pulled into the cavity 476 is not lost to the surrounding environment through the spacers 425. As will be further appreciated, one or more sensor devices can be spaced from the orifice 423 via a flow channel, which can also be provisioned with deposition or bonding processes. The hermetic seal is created by the wafer bonding process. For instance, in the case of a silicon membrane 427 bonded to a silicon oxide spacer material, the seal formed by bonding is hermetic. In another embodiment, if an epoxy seal is used, the hermetic property of that bond would be independent of the spacer material which could be ceramic/silicon, such as in the case of a ceramic/silicon cap that includes the baffle and side walls. As will be further appreciated, there are many ways the flow channel can be formed, such as 3D printing, molded plastics, etched PCB trench, etched semiconductor substrate, etched metal, and micro-machining, and any combinations of such forming techniques. Numerous suitable fabrication schemes will be apparent in light of this disclosure.

Fabrication Methodology

An example process flow to fabricate the device described with reference to FIG. 4 is shown in FIGS. 5a-k, where the conductive membrane 427 is formed from the highly doped device layer of a semiconductor-on-insulator (SOI) wafer. In one such embodiment, assume the SOI wafer comprises a single crystal silicon layer on an oxide layer example, which is particularly advantageous due to the higher quality factor (Q) and therefore better energy efficiency of using single crystal silicon as the membrane material (as opposed to, for example, a polycrystalline material). The flow of FIGS. 5a-k also shows an example of the upper cavity fabrication via wafer bonding. The sensor can also be formed in advance and then spaced from the orifice by way of an intervening flow channel deposited or otherwise formed proximate to the upper cavity layer. A gap between the orifice and the flow channel provides access to ambient air/fluid in order to pull it into the cavity and subsequently expel to entrain the surrounding ambient air/fluid. Thus, specific materials and process flows for how to fabricate a synthetic jet sensing system are provided. However, other materials and processing techniques can be used to form the various parts of the structure (e.g., lower cavity, upper cavity, sensing layer, whether they are grown or otherwise formed on each other or otherwise coupled to one another in a working fashion), as will be appreciated in light of this disclosure.

Figure 5A:
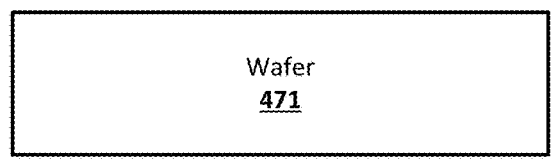
FIGS. 5a-k collectively illustrate a methodology for making a synthetic jet device based sensing system including the various intermediate and resulting structures, in accordance with an embodiment of the present disclosure.
Figure 5B:
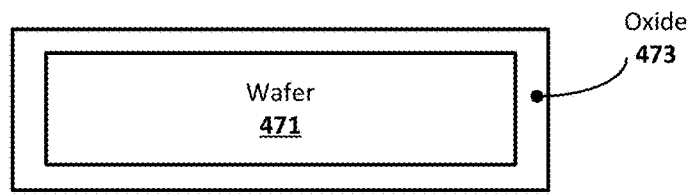
Figure 5C:
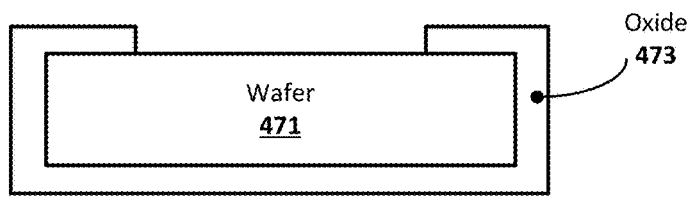
Figure 5D:
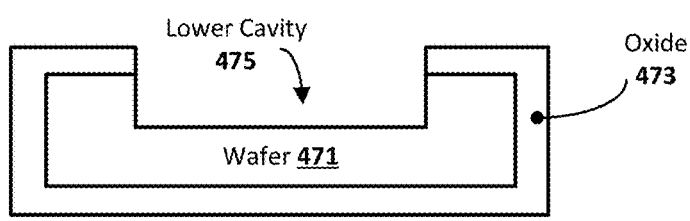

In more detail, FIG. 5a shows a silicon wafer 471 that has been highly doped. In one example embodiment the dopant is boron, although other suitable dopants can be used as well (e.g., arsenic, phosphorus, and gallium). FIG. 5b shows the doped silicon wafer 471 with an oxide layer 473 formed thereon. Note that while oxide is shown on all walls of the cross section, in other embodiments it may only be provided on the top surface, or otherwise selectively provided. In one example case, a silicon dioxide layer can be formed by exposing the doped silicon substrate 471 to an oxygen flow. The thickness of the oxide 473 can be governed by process parameters such as the exposure time, temperature and pressure. As will be appreciated in light of this disclosure, the doped silicon wafer 471 provides the lower conductor 431 and the oxide layer provides the non-conductive lower spacer 429 between the lower conductor 431 and the membrane 427. FIG. 5c shows how the resulting structure can then be patterned and etched to remove oxide in the cavity region to be formed, and FIG. 5d shows the resulting lower cavity 475 after the silicon etch. Conventional patterning and etch techniques can be used.

Figure 5E:
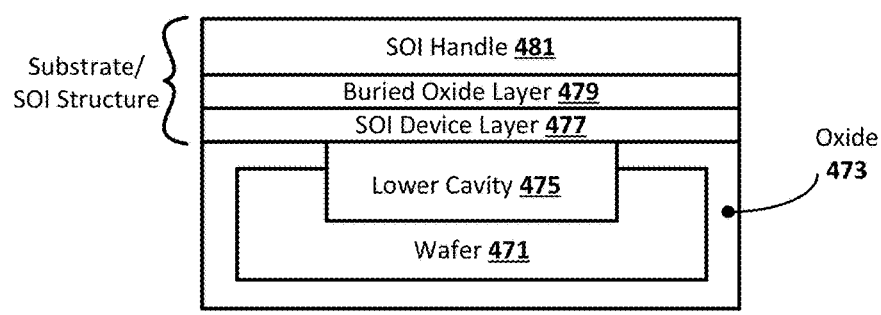
Figure 5F:
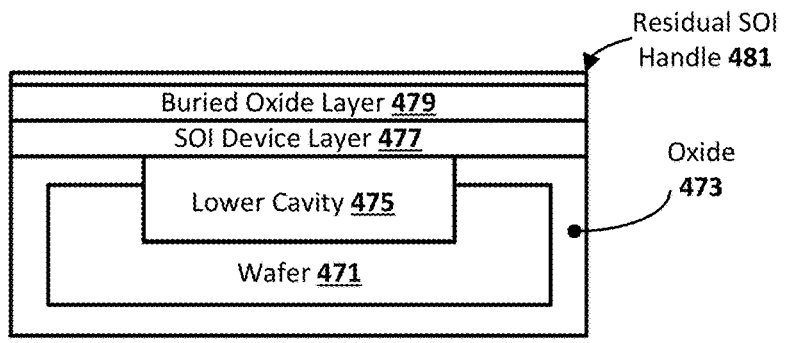
Figure 5G:
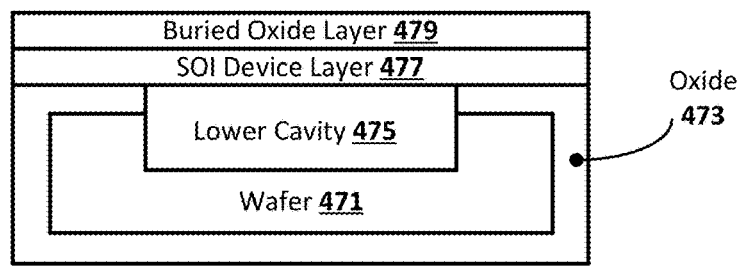

The process flow continues with fusion bonding a SOI wafer to the structure, as shown in FIG. 5e. As can be seen, the SOI structure or substrate includes a SOI device layer 477 (e.g., single crystal silicon layer), a buried oxide layer 479 (e.g., silicon dioxide layer), and a SOI handle 481 (e.g., bulk silicon layer). FIG. 5f shows the resulting structure after the majority of the SOI handle 481 is removed, which can be accomplished via a chemical mechanical planarization (CMP) process, and FIG. 5g shows the resulting structure after the remainder of the SOI handle 481 is removed to expose the underlying buried oxide layer 479, which can be accomplished using any number of conventional etch processes commonly used on silicon (wet and/or dry, anisotropic and/or isotropic).

Figure 5H:
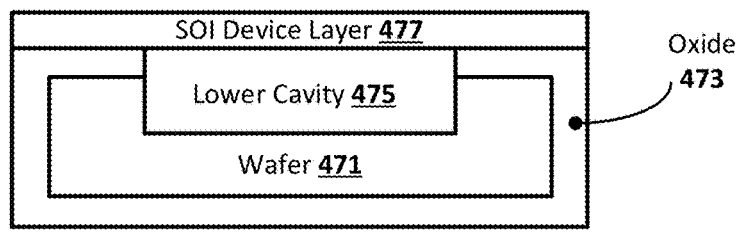

FIG. 5h shows the resulting structure after the buried oxide layer 479 is etched away to release the SOI device layer 477. Again, any suitable etching schemes can be used. As will be appreciated, the SOI device layer 477 provides the actuated membrane 427, which can be patterned with a metal or otherwise metalized to provide a first electrode, as can be the wafer 471 to provide the other electrode. In some embodiments, further note that layers of different materials may be used to form the electrode. As previously explained, an AC bias voltage can be applied across the two electrodes to activate the membrane so that it vibrates at its resonant frequency to provide the movement/puffs.

Figure 5I:
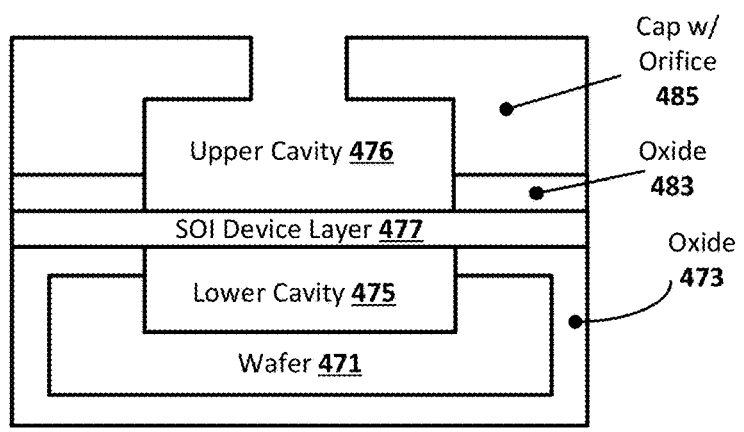

FIG. 5*i* shows the resulting structure after a pre-etched ceramic cap or silicon wafer 485 is fusion bonded to the SOI device layer 477 to form the upper cavity 476. In one such case, the oxide 483 is formed on the cap 485 prior to bonding or is otherwise part of the cap 485. As will be appreciated, the pre-etched cap/wafer 485 provides the baffle 421 having the orifice 423, and the oxide 483 provides the upper non-conductive spacer 425. In one particular embodiment, a single element provides the combination of the oxide 483 and cap with orifice 485, so as to provide the resulting structure/geometry of the baffle 421, orifice 423, and upper spacer 425. In this sense, baffle 421 is effectively the top of the cap 485 and the upper spacer 425 is effectively the bottom of the cap 485 with the oxide 483. For example, the top of cap 485 and the spacer 425 can be formed of a non-conductive ceramic, and the seal between the cap 485 and wafer is made with epoxy. In such a case, there is no need for oxide layer 483. In still other embodiments, the spacers 425 can be part of the buried oxide layer 479 that is masked and left behind during the buried oxide (BOX) etch process shown in FIG. 5*h*, assuming that layer 479 has the appropriate geometry for the target application. In still other embodiments, the oxide layer 483 can be deposited or otherwise formed directly on the SOI device layer 477, and then a pre-etched cap 485 (just the baffle portion, rather than both the lower spacer portion and the upper baffle portion) could be bonded in place. Alternatively, the pre-etched cap 485 can be formed directly on the oxide layer 483 using a sacrificial material to define the upper cavity 476. Further note that the cap 485 and oxide 483 need not actually be an oxide, but can be any other suitable material as previously explained. To this end, the depicted process flow is one example embodiment, and numerous other material sets and structures and forming techniques will be apparent in light of this disclosure.

Figure 5J:
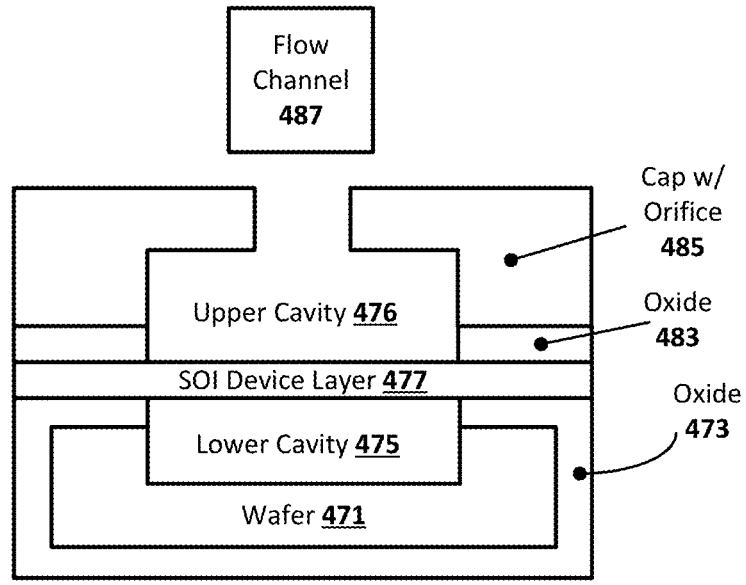
Figure 5K:
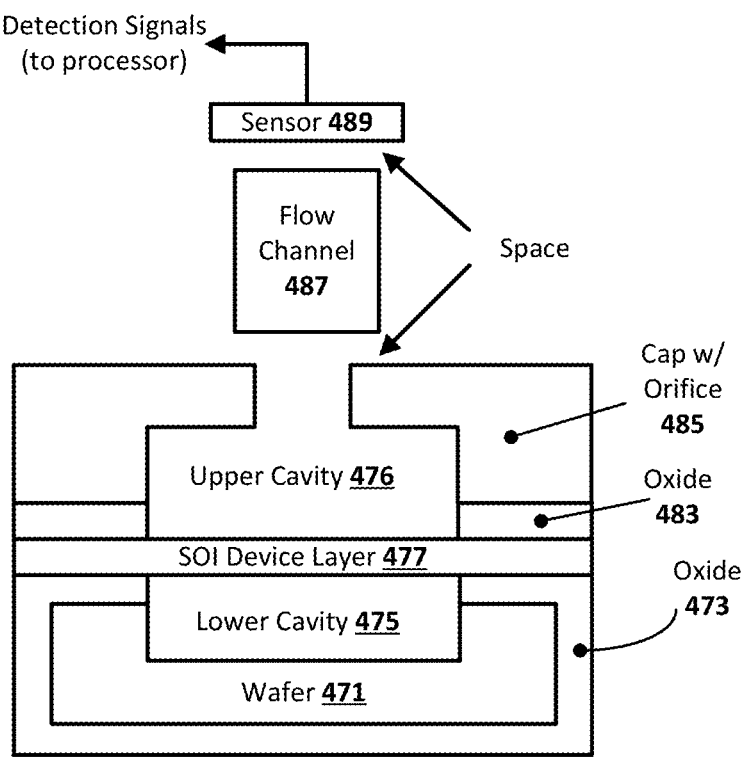

The resulting synthetic jet structure can then be operatively coupled with a preformed sensor layer via a flow channel 487. For example, a flow channel 487 can be deposited proximate the cap 485, as shown in FIG. 5*j*. Note the gap between the cap 485 and the flow channel 487 allows for the ambient air/fluid to be entrained as previously explained. A preformed sensor 489 (e.g., wafer or other suitable substrate with sensor circuit formed thereon) can be bonded to or otherwise operatively spaced from the flow channel 487 after the flow channel is etched or otherwise formed. In some embodiments, a space between the flow channel 487 and the sensor 489 allows for the jet flow to pass by the sensor as the sensor samples that flow. Another embodiment is the case where the synthetic jet device(s) are placed inside the flow channel 487 as long as the flow channel is larger than the synthetic jet device(s). This will also allow for entrainment of surrounding air/fluids. In other embodiments where the flow channel 487 and the sensor 489 are directly coupled, flow channel vents or ports to either side of the sensor may be provisioned to allow for release or pass-thru of the sampled jet flow. One example resulting structure is shown in FIG. 5*k*. As can be further seen, detection signals can be read out or otherwise provided from the sensor layer and provided for subsequent analysis and processing as previously explained. Some embodiments may further include an intervening readout circuit to amplify and/or filter the detection signals prior to sending those signals for processing.

Figure 5Q:
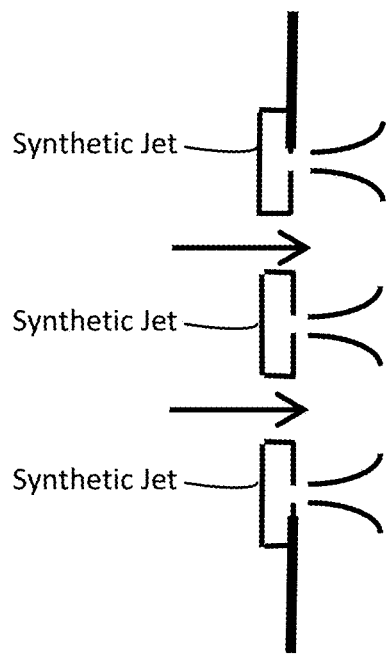
Figure 5R:
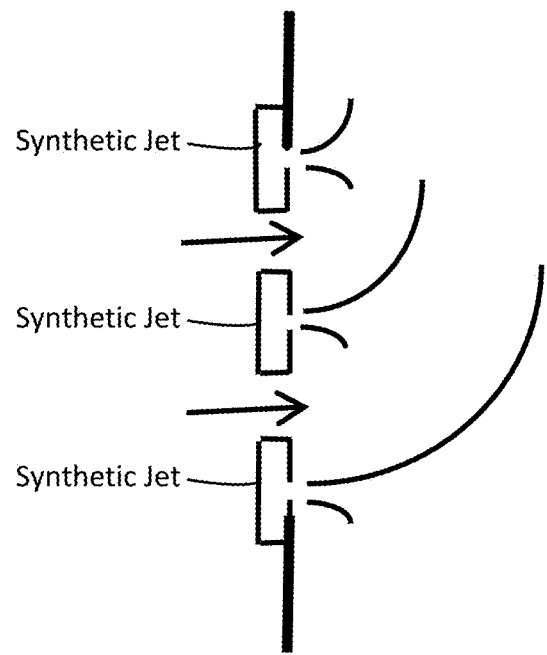

Note that FIGS. 5*a-k* are not drawn to any particular scale, and that the flow channel does not have to be larger than the synthetic jet device. As will be further appreciated, there may be more than one device per flow channel. For example, FIG. 5*l* shows another embodiment where the synthetic jet device is inside the flow channel proximate one end. FIG. 5*m* shows another example configuration where the synthetic jet device is inside the flow channel, but further inside the flow channel and on a sidewall of the flow channel. FIG. 5*n* is similar to the example configuration of FIG. 5*m*, except that the synthetic jet device is outside the flow channel and accesses the flow channel via an orifice in the sidewall. FIG. 5*o* shows another example configuration where a plurality of synthetic jet devices (three in this example case), with one jet device proximate the input of the flow channel, and two more jet devices outside the flow channel and that access the flow channel via respective orifices in the sidewall(s). FIG. 5*p* is similar to the example configuration of FIG. 5*o*, except that the jet device proximate the input of the flow channel is now inside the flow channel. Thus, note that jet devices may be both inside and outside of the flow channel, in some embodiments. Further note that the flow channel can have any geometric shape and need not be cylindrical. For instance, it can be square, triangular, rectangular, or elliptical, to name a few suitable shapes. To this end, any reference to sidewall or sidewalls is not intended to limit this disclosure to any particular shape. Further note that in cases where there are multiple synthetic jet devices, they need not have the same output. For example, the example embodiment of FIG. 5*q* includes a plurality of jet devices all driven by a common drive signal to provide an in-phase operation, while the example embodiment of FIG. 5*r* employs driver signals that are phase shifted to provide a phase-shifted operation. This means that the synthetic jet devices do no expel puffs of air at the same time; rather, they are shifted in time. This result in that the synthetic jet devices flow can be directed (e.g., up or down, in this example). As will be appreciated, note that the entrained air/fluid is depicted with arrows in FIGS. 5*l-r*. Any other flow channel and jet configurations can be used as well, as will be appreciated.

Numerous variations will be apparent in light of this disclosure. For example, in other embodiments the membrane 427 (device layer 477) is implemented using piezoelectric materials (e.g., aluminum nitride, barium titanate, lead zirconate titanate) or electromagnetics, in lieu of an electrostatic membrane. In the piezoelectric case, note that the membrane 427 could be, for example, made of any material such as silicon or silicon oxide with piezoelectric material deposited thereon. In the electromagnetic case, note that the membrane 427 could be, for example, made of a conductive material such as metal, and a permanent magnet could be embedded above or below the membrane to provide a magnetic field at the membrane location. Alternatively, the membrane 427 can be nonconductive and the magnet could be attached to it and actuated by applying an external time varying magnetic field. In a more general sense, the synthetic jet device included in the sensing system can be implemented with any transducer technology that is capable of actuating to create a synthetic jet flow that entrains ambient air/fluid for purposes of providing that entrained air/fluid to a sensing region in a controlled delivery. Also, note that the example embodiment depicted in FIG. 5*e-g* employs a SOI wafer to create a thin layer of bonded silicon 477 for the membrane 427. An alternative approach that may be better suited for high volume manufacturing may be to bond a silicon wafer to the cavity wafer shown in FIG. 5*d*, and to use ion implantation and layer splitting to define and form a thin silicon layer. In addition, FIG. 5*i* shows an oxide based fusion bond as one method for bonding a silicon cap 485 to the silicon membrane surface. An alternative would be to use a ceramic cap with an epoxy bond. In such an example case, the oxide layer 483 may not be needed—as long as the baffle is non-conductive or it is otherwise electrically isolated from the silicon membrane of device layer 477. Additionally, note that the inner diameter of the cap 485 upper cavity 476 does not need to match the diameter of the membrane layer 477 diameter. For instance, the inner diameter of the upper cavity 476 can be larger than the membrane layer 477 diameter. In addition, the example embodiment in FIGS. 5a-k show only one die on the wafer surface for purposes simplicity, but other embodiments may include multiple die.

As will be further appreciated, the techniques can be used to provide sensing solutions for integration with any number of computing platforms, or to provide standalone sensor solutions, or to provide micro-scale pumping applications. Further note that while embodiments show the orifice of the synthetic jet opposite the membrane, note that other embodiments may have the orifice elsewhere such as to one side of the cavity rather than at the end of the cavity opposite the orifice. Nor does the orifice need to be centered or otherwise put in a particular position. For instance, in one example embodiment, and with further reference to FIG. 4, the orifice 423 can be in or otherwise replace the right spacer 425, and the orifice 423 at the top can be closed off. Numerous other such variations will be apparent in light of this disclosure.

Distributed Sensing System

Figure 6:
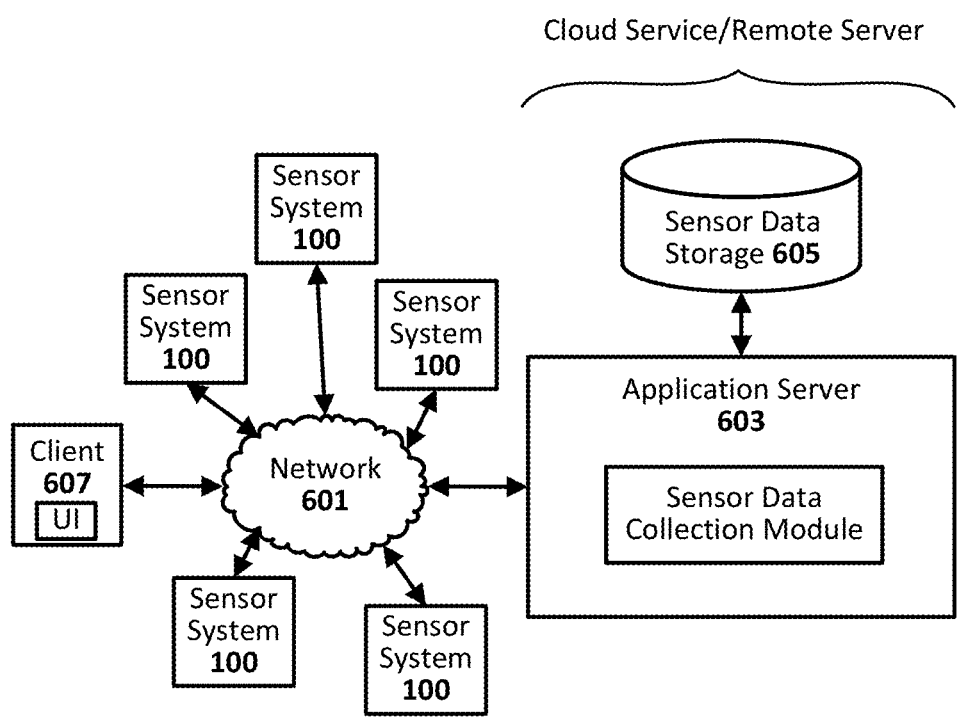
FIG. 6 illustrates a distributed sensor system configured in accordance with an embodiment of the present disclosure.

FIG. 6 illustrates a distributed sensor system configured in accordance with an embodiment of the present disclosure. As can be seen, the system includes a plurality of synthetic jet based sensing systems 100 communicatively coupled to a network 601. An application server 603 capable of executing a sensor data collection module is configured to access the various sensor systems 100 to obtain detection levels from each. Sensor data received by the server 603 can be stored in sensor data storage 605. Likewise, one or more client computing systems 607 may also be able to access one or more of the sensor systems 100 (e.g., by way of a subscription to a cloud-based environmental sensing system or some other authorized usage).

The network 601 can be any communication network or combination of networks, such as the Internet and one or more local access networks. Wireless and wired network technologies can be used, as will be appreciated. While only one client 607 and one server 603 are shown, it will be appreciated that any number of clients 607 and servers 603 may be included in the system, as needed. Each client 607 and server 603 can be implemented with any suitable computing architecture, as commonly done, and programmed or otherwise configured to execute data collection from the distributed sensor system. The server(s) 603 can be, for example, part of a cloud-based sensing system, such as an environmental monitoring system that has sensors deployed in various cities and/or other locations around the world or country or campus or laboratory (depending on the scope and purpose of the system), so that users (e.g., travelers, government agencies, lab workers, or other interested parties) can access the system to determine if target feature levels local to an area are acceptable or otherwise as expected. The user interface (UI) of the client computing system 607 may be, for example, similar to the one shown in FIG. 2, although any number of suitable UI schemes can be used. As will be further appreciated, similar UI schemes can also be used with respect to the application server 603 and to provide access to the storage 605, for both writing data to that storage and reading data from that storage.

Such an embodiment may be implemented, for example, in the context of a so-called Internet of Things (IoT) configuration to provide the one or more sensor nodes 100 or other such distributed sensor system. Further note that in such an IoT system, the device could be integrated in a fixed sensor node deployed at a particular location. To this end, the sensor systems 100 need not be mobile. Further note that the sensor systems 100 can be addressable like any other computing system on a given network, such as by a given IP address, MAC address, and/or any other suitable addressing mechanism by which an element on a given network can be accessed. Numerous variations and embodiments employing a distributed sensing system will be apparent in light of this disclosure.

FURTHER EXAMPLE EMBODIMENTS

The following examples pertain to further embodiments, from which numerous permutations and configurations will be apparent.

Example 1 is a sensing system. The sensing system includes a flow channel, and a synthetic jet device comprising a vibrating membrane in a cavity with an orifice that outputs to the flow channel. The synthetic jet is configured to entrain surrounding air/fluid into the flow channel to provide a jet flow. The system further includes a sensor for receiving the jet flow from the flow channel and configured to detect a target feature included in the jet flow.

Example 2 includes the subject matter of Example 1, wherein each of the flow channel, synthetic jet, and sensor are implemented with discrete components populated on a substrate (e.g., printed circuit board or other suitable substrate).

Example 3 includes the subject matter of Example 2, wherein the substrate populated with the channel, synthetic jet, and sensor is within a housing or package.

Example 4 includes the subject matter of Example 1, wherein each of the flow channel, synthetic jet, and sensor are implemented as an integrated circuit.

Example 5 includes the subject matter of Example 4, wherein the integrated circuit configured with the channel, synthetic jet, and sensor is within a housing or package.

Example 6 includes the subject matter of any of the previous Examples, wherein the sensor includes at least one of an optical sensor, a microelectromechanical systems resonance sensor, an electromechanical sensor, a metal oxide sensor, an electrochemical sensor, a radiation sensor, a pollutant sensor, and a gas sensor. Any number of other sensors may be used, as will be appreciated.

Example 7 includes the subject matter of any of the previous Examples, wherein the target feature is an air pollutant.

Example 8 includes the subject matter of any of the previous Examples, wherein the target feature is at least one of particulate matter, ground-level ozone, carbon monoxide, a sulfur oxide, a nitrogen oxide, and lead.

Example 9 includes the subject matter of any of the previous Examples, wherein the system includes multiple sensors. In some such cases, each sensor is configured to sense a different target feature.

Example 10 includes the subject matter of any of the previous Examples, wherein the system includes multiple synthetic jets.

Example 11 includes the subject matter of any of the previous Examples, wherein the system includes multiple flow channels.

Example 12 includes the subject matter of any of the previous Examples, wherein the system includes multiple synthetic jets each coupled to one or multiple sensors via a corresponding flow channel. The flow channel may be multiple distinct flow channels, or a common flow channel that has a split output of two or more outputs.

Example 13 includes the subject matter of any of the previous Examples, wherein the vibrating membrane comprises single crystal silicon.

Example 14 includes the subject matter of any of the previous Examples, the system further including a processor configured to issue an alert in response to the target feature being detected by the sensor.

Example 15 includes the subject matter of Example 14, the system further including at least one of: a display to visually present the alert to a user; a haptic element to present the alert to the user; and a speaker to aurally present the alert to the user.

Example 16 includes the subject matter of Example 15, wherein the display is a touch screen display.

Example 17 includes the subject matter of any of the previous Examples, the system further including a user interface configured to present detection information in response to the target feature being detected.

Example 18 includes the subject matter of Example 17, wherein the user interface provides a visual presentation of the detection information.

Example 19 includes the subject matter of Example 17, wherein the user interface provides an aural presentation of the detection information.

Example 20 includes the subject matter of any of Examples 17-19, wherein the detection information comprises at least one of a pass/fail status of the target feature, a concentration level of the target feature, a geolocation of the target feature, and a time of detection.

Example 21 is a system-on-chip (SOC) comprising the system of any of the previous Examples.

Example 22 is a mobile computing device comprising the system of any of the previous Examples.

Example 23 includes the subject matter of Example 22, wherein the mobile computing device is one of a wearable device, smartphone, tablet, or laptop computer.

Example 24 is at least one non-transient computer program product encoded with instructions that when executed by one or more processors cause a process to be carried out. The process includes receiving a detection signal associated with a target feature detected by a synthetic jet sensing system, the target feature being detected in ambient air around the synthetic jet sensing system, and determining if the detection signal indicates a given threshold for the target feature has been exceeded. In response to determining that the threshold has been exceeded, the process continues with causing an alert to be issued.

Example 25 includes the subject matter of Example 24, wherein the detection signal is binary in nature, having either a first state indicating a pass status with respect to the target feature or a second state indicating a fail status with respect to the target feature.

Example 26 includes the subject matter of Example 24, wherein the detection signal comprises a voltage level indicating a concentration level of the target feature detected.

Example 27 includes the subject matter of any of Examples 24-26, wherein in response to determining that the threshold has not been exceeded, the process comprises continuing monitoring for presence of the target feature.

Example 28 includes the subject matter of Example 27, wherein continuing monitoring for presence of the target feature includes periodically monitoring according to a predefined sampling schedule.

Example 29 includes the subject matter of Example 27 or 28, wherein continuing monitoring for presence of the target feature includes periodically monitoring based on movement of a user from one geographic location to another.

Example 30 includes the subject matter of any of Examples 24-29, wherein the alert is presented visually via a display screen.

Example 31 includes the subject matter of any of Examples 24-30, wherein the alert is presented aurally via a speaker.

Example 32 includes the subject matter of any of Examples 24-31, wherein the process further comprises logging the alert and associated data in an electronic storage facility.

Example 33 includes the subject matter of Example 32, wherein the associated data comprises at least one of date of detection, time of detection, geo-location of detection, and amount of the target feature detected.

Example 34 includes the subject matter of Example 32 or 33, wherein the electronic storage facility is remote to the synthetic jet sensing system.

Example 35 includes the subject matter of Example 32 or 33, wherein the electronic storage facility is local to the synthetic jet sensing system.

Example 36 includes the subject matter of any of Examples 32-35, wherein logging the alert and associated data comprises automatic reporting of the detection and related data to a central authority or governmental agency.

Example 37 is a sensing device. The device includes a synthetic jet including a bottom conductor spaced from a membrane so as to provide a lower cavity, and a baffle having an orifice spaced from an opposing side of the membrane to provide an upper cavity, wherein the membrane vibrates in response to a bias applied across the membrane and bottom conductor so as to create a jet flow at the orifice output. The device further includes a flow channel to receive the jet flow, and a sensor to receive the jet flow from the flow channel and to detect a target feature in the jet flow.

Example 38 includes the subject matter of Example 37, wherein the device is a semiconductor device.

Example 39 includes the subject matter of Example 37 or 38, wherein the bottom conductor comprises a non-conductive material having a metal electrode thereon.

Example 40 includes the subject matter of any of Examples 37-39, wherein the membrane comprises a non-conductive material having a metal electrode thereon.

Example 41 includes the subject matter of any of Examples 37-40, wherein the membrane comprises single crystal silicon.

Example 42 includes the subject matter of any of Examples 37-41, wherein the membrane comprises piezoelectric material.

Example 43 includes the subject matter of any of Examples 37-41, wherein the membrane comprises an electromagnetically actuated material.

Example 44 includes the subject matter of any of Examples 37-41, wherein the membrane comprises an electrostatic membrane.

The foregoing description of example embodiments has been presented for the purposes of illustration and description. It is not intended to be exhaustive or to limit the present disclosure to the precise forms disclosed. Many modifications and variations are possible in light of this disclosure. It is intended that the scope of the present disclosure be limited not by this detailed description, but rather by the claims appended hereto. Future filed applications claiming priority to this application may claim the disclosed subject matter in a different manner, and may generally include any set of one or more limitations as variously disclosed or otherwise demonstrated herein.

What is claimed is:

1. A sensing system, comprising:
   a flow channel;
   a synthetic jet device comprising
      a first cavity,
      a second cavity having a single orifice,
      a membrane between the first and second cavities,
      a first structure adjacent to the first cavity,
      a second structure adjacent to the second cavity,
      a first insulator spacer between the first structure and the membrane, the first insulator spacer absent between the first cavity and the membrane, and
      a second insulator spacer between the second structure and the membrane,
      wherein the single orifice of the second cavity outputs to the flow channel, the synthetic jet device configured to entrain surrounding air/fluid into the flow channel to provide a known or controlled jet flow when the membrane vibrates; and
   a sensor for receiving the jet flow from the flow channel and configured to detect a concentration of a target feature included in the jet flow.

2. The system of claim 1 wherein each of the flow channel, synthetic jet device, and sensor are implemented with discrete components populated on a substrate.

3. The system of claim 2 further comprising a housing or package containing the substrate.

4. The system of claim 1 wherein the sensor includes at least one of an optical sensor, a microelectromechanical systems resonance sensor, an electromechanical sensor, a metal oxide sensor, an electrochemical sensor, a radiation sensor, a pollutant sensor, and a gas sensor.

5. The system of claim 1 wherein the target feature is at least one of particulate matter, ground-level ozone, carbon monoxide, a sulfur oxide, a nitrogen oxide, lead, and an air pollutant.

6. The system of claim 1 wherein the system includes multiple sensors each configured to sense a different target feature.

7. The system of claim 1 wherein the system includes multiple synthetic jets.

8. The system of claim 1 wherein the membrane consists of a single material layer between the first and second cavities.

9. The system of claim 1 wherein the membrane comprises single crystal silicon.

10. The system of claim 1 further comprising at least one of:
    a processor configured to issue an alert in response to the concentration of the target feature being detected by the sensor;
    a display to visually present the alert to a user;
    a haptic element to present the alert to the user;
    a speaker to aurally present the alert to the user; and
    a user interface configured to present detection information in response to the target feature being detected.

11. The system of claim 10 wherein the user interface provides at least one of a visual presentation of the detection information and an aural presentation of the detection information.

12. The system of claim 10 wherein the detection information comprises at least one of a pass/fail status of the target feature, a concentration level of the target feature, a geolocation of the target feature, and a time of detection.

13. A mobile computing device comprising the system of claim 1.

14. The system of claim 1 wherein the first structure is a bottom conductor spaced from the membrane so as to provide the first cavity, and the second structure is a baffle having the single orifice spaced from an opposing side of the membrane to provide the second cavity, wherein the membrane vibrates in response to a bias applied across the membrane and bottom conductor so as to create a jet flow out of the single orifice.

15. The system of claim 14 further comprising a substrate and a housing or package, wherein the substrate is within the housing or package.

16. The system of claim 1 wherein the synthetic jet device is capable of controlling the jet flow by altering at least one of amplitude, drive signal, oscillation frequency, and oscillation shape of the membrane.

17. The system of claim 1 wherein the first cavity is completely enclosed.

18. A sensing system, comprising:
    a flow channel;
    a synthetic jet device comprising
       a first cavity,
       a second cavity having a single orifice,
       a membrane between the first and second cavities,
       a first structure adjacent to the first cavity,
       a second structure adjacent to the second cavity,
       a first insulator spacer between the first structure and the membrane, and
       a second insulator spacer between the second structure and the membrane, the second insulator spacer absent between the second cavity and the membrane,
       wherein the single orifice of the second cavity outputs to the flow channel, the synthetic jet device configured to entrain surrounding air/fluid into the flow channel to provide a known or controlled jet flow when the membrane vibrates; and
    a sensor for receiving the jet flow from the flow channel and configured to detect a concentration of a target feature included in the jet flow.

19. The system of claim 18 wherein each of the flow channel, synthetic jet device, and sensor are implemented with discrete components populated on a substrate.

20. The system of claim 18 wherein the sensor includes at least one of an optical sensor, a microelectromechanical systems resonance sensor, an electromechanical sensor, a metal oxide sensor, an electrochemical sensor, a radiation sensor, a pollutant sensor, and a gas sensor.

21. The system of claim 18 wherein the target feature is at least one of particulate matter, ground-level ozone, carbon monoxide, a sulfur oxide, a nitrogen oxide, lead, and an air pollutant.

22. A sensing system, comprising:
    a flow channel;
    a synthetic jet device comprising a first cavity,
    a second cavity having a single orifice,
    a membrane between the first and second cavities, with no other intervening layers between the first and second cavities, a first structure adjacent to the first cavity, a second structure adjacent to the second cavity,
    a first insulator spacer between the first structure and the membrane, and a second insulator spacer between the second structure and the membrane, wherein the single orifice of the second cavity outputs to the flow channel, the synthetic jet device configured to entrain surrounding air/fluid into the flow channel to provide a known or controlled jet flow when the membrane vibrates; and a sensor for receiving the jet flow from the flow channel and configured to detect a concentration of a target feature included in the jet flow.

23. The system of claim 22 wherein each of the flow channel, synthetic jet device, and sensor are implemented with discrete components populated on a substrate.

24. The system of claim 22 wherein the sensor includes at least one of an optical sensor, a microelectromechanical systems resonance sensor, an electromechanical sensor, a metal oxide sensor, an electrochemical sensor, a radiation sensor, a pollutant sensor, and a gas sensor.

25. The system of claim 22 wherein the target feature is at least one of particulate matter, ground-level ozone, carbon monoxide, a sulfur oxide, a nitrogen oxide, lead, and an air pollutant.

* * * * *